US006991811B1

(12) United States Patent
Brovelli et al.

(10) Patent No.: US 6,991,811 B1
(45) Date of Patent: Jan. 31, 2006

(54) *ECHINACEA* INDUCTION OF PHASE II ENZYMES

(75) Inventors: Ernesto A. Brovelli, Corona, CA (US); Yong Qian, San Diego, CA (US); Puri G. David, Moreno Valley, CA (US); Kari L. Truax, Hemet, CA (US); Yingqin Li, Murrieta, CA (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 09/575,307

(22) Filed: May 19, 2000

(51) Int. Cl.
*A61K 35/78* (2006.01)
(52) U.S. Cl. .................................................. 424/725
(58) Field of Classification Search ................ 424/737, 424/773, 725
See application file for complete search history.

(56) References Cited

U.S. PATENT DOCUMENTS

| 4,857,512 | A | 8/1989 | Wagner et al. ................. 514/54 |
| 5,401,502 | A | 3/1995 | Wunderlich et al. ...... 424/195.1 |
| 5,578,307 | A | 11/1996 | Wunderlich et al. ...... 424/195.1 |
| 5,876,728 | A | 3/1999 | Kass et al. ................ 424/195.1 |
| 5,939,071 | A | 8/1999 | Joseph ...................... 424/195.1 |
| 6,096,307 | A * | 8/2000 | Braswell et al. ............ 424/94.1 |
| 6,217,878 | B1 * | 4/2001 | Menon et al. ............ 424/195.1 |
| 6,440,448 | B1 * | 8/2002 | Intelisano |
| 2002/0028258 | A1 * | 3/2002 | Mitschev et al. |
| 2002/0132021 | A1 * | 9/2002 | Raskin et al. |

FOREIGN PATENT DOCUMENTS

WO    WO 99/21007    4/1999

OTHER PUBLICATIONS

The Condensed Chemical Dictionary, 10th Edition, 1981, p. 237.*
Dorland's Illustrated Medical Dictionary, 27th edition, 1988, p. 943.*
Facino et al., IL Farmaco, 48, (10), 1447-1461, 1993.*
*Tumor Inhibitors 3. Identification and Synthesis of an Oncolytic Hydrocarbon From American Coneflower Roots*; Denys J. Voaden and Martin Jacobson; Journal of Medicinal Chemistry, 1972, vol. 15, No. 6, pp. 619-623. (Abstract only).
Chemical Abstract vol. 47, p. 6048, *The Influence of Echinacea Purpurea Upon the System Hypophysis-Adrenals*; E. Koch and H. Uebel (Biol. Inst. Dr. Madaus, Cologne-Merheim, Ger.) Arneimittel-Forsch 3, 133-7 (1953). (Abstract only).
Chemical Abstract vol. 53, p. pp. 8550-8551, *Recovery of Active Agents from Aqueous Extracts of the Species of Echinacea*, Chemie Grunenthal G.m.b.H. (Herbert Keller, Inventor). Ger. 950,674, Oct. 11, 1956. (Abstract only).

Chemical Abstract vol. 56, p. 7444, *Physiological Active Solutions from Echinacea Extracts*; Frithjof Martin. Ger. (East) 21, 788, Appl. Dec. 12, 1958.
Chemical Abstract No. 68: 2529g, *Polyacetylene Compounds in Echinacea Purpurea and E. Angustifolia*, K.E. Schulte, G. Ruecker, and J. Perlick (Westfaelischen Wilhelms-Univ., Muenster, Ger.), Arzneim-Forsch 17(7), 825-9 (1967)(Ger). (Abstract only).
Chemical Abstract No. 90: 43820t, *Pharmaeuticals Containing Lactic Acid Derivatives and Echineacea*, Reith, Franz Josef Ger. Offen. 2,721,014 16, Nov. 1978, Appl. May 10, 1977; 10 pp. (Atstract only).
Chemical Abstract No. 97: 74281s, *Low-Molecular-Weight Polysaccharides from Plants of Composite Families and Pharmaceuticals Compositions Containing Them*, Wagner, Hildebert; Stickl, Helmut; Drews, Juergen; Proksch, Angelika, Ger. Offen. DE 3,042,491, Jul. 15, 1982, Appl Nov. 22, 1980; 18 pp. (Abstract only).
Chemical Abstract No. 107: 12902m, *Isolation of Sesquiterpene Derivatiaves and pharmaceuticals Containing Thses Compounds*, Wagner, Hildebert; Bauer, Rudolf; Ott, Hoger, (LOMAPHARM, Rudolf Lohman M.m.b.H. K-G Pharmazeutische Fabrik) Ger. Offen. DE 3,522,075, Jan. 2, 1987, Appl. Jun. 20, 1985; 8 pp. (Abtract only).
Chemical Abstract No. 108: 173417t, *Echinaccea. Comparative TLC and HPLC Analysis of Herbal Drugs from Echinacea Purpurea, E. Pallida and E. Angustifolia. Part 3*, Bauer, Rudolf; Remiger, Peter; Wagner, Hildebert (Inst. Pharm. Biol., Univ. Muenchen, D-800 Munich, 2 Fed. Rep. Ger.) Dtsch, Apoth. Ztg. 1988, 128(4), 174-80 (Ger). (Abstract only).
Chemical Abstract No. 109:L 27600b, *Polysaccharides Derived from Echinacea Plants as Immunostimulants*, Wagner, Hildebert; Zenk, Meinhart H; Ott, Holger (LOMAPHARM, Rudolf Lohman G.m.b.H. K.-g. Pharmazeutische Fabrik) Ger. Offen. DE 3,541,945 Jun. 4, 1987, Appl. Nov. 27, 1985; 10 pp. (Abstract only).
Chemical Abstract No. 112: 210981c, *Immunostimulant Echinacea Extracts Containing Carboxylic Acid Isobutylamides, Oxoalkenes and Oxoalkynes*, Bauer, Rudolf; Wagner, Hildebert (LOMAPHARM, Rudolf Lohmann G.m.b.H. K-G. Pharmazeutische Fabrik) Ger. Offen. DE 3,744,571, Jul. 13, 1989, Appl. Dec. 30, 1987; 10 pp. (Abstract only).

(Continued)

*Primary Examiner*—Michael Meller
(74) *Attorney, Agent, or Firm*—Alticor Inc.

(57) ABSTRACT

The present invention relates to the use of *Echinacea* as a cancer chemopreventive agent to block the formation of and to detoxify cancer-causing agents, or carcinogens. More particularly, the present invention relates to the induction of phase II enzymes by *Echinacea*, and specifically by lipid-soluble fractions isolated from *Echinacea*. The present invention also contemplates a novel method of extracting the desired lipid-soluble fractions from *Echinacea*.

3 Claims, 2 Drawing Sheets

OTHER PUBLICATIONS

Chemical Abstract No. 117: 11849y, *Therapeutic Extracts of Ecinaccea Purpurea*, Etsuio, Bonbaruderi; Enriko, Furanji (Indena S.p.A.) Jpn. Kokai Tokkyo Koho JP 04 82,838, [92 82,838], Mar. 16, 1992, Appl. 90/196,383, Jul. 26, 1990; 5 pp. (Abstract only).

Chemical Abstract No. 123: 82077a *Separation of Solvents from Fluid Mixtures in the Food and Drug Industries*, Mauz, Matthias Ger. Offedn DE 4,326,842, Feb. 16, 1995, Appl. Aug. 10, 1993; 7 pp. (Abstract only).

Chemical Abstract No. 123: 237834w, *Transdermal Patch for Release of Active Agents from Hot-Melt Adhesives*, Hoffmann, Hans-Rainer; Roreger, Micheal (ITs Lohmann Therapie-Systeme GmbH und Co. KG) Ger. DE 4,416,927 Aug. 31, 1995, Appl. May 13, 1994; 14 pp. (Abstract only).

Chemical Abstract No. 126: 166218x *In Vitro of Echinacea and Ginseng on Natural Killer and Antibody-Dependent Cell Cytotoxcity in Health Subjects and Chronic Fatigue Syndrome or Acquired Immunodeficiency Syndrome Patients*, See, Darryl M.; Broumand, Nikki; Sahl, Lisa; Tilles, Jeremiah G. (Department of Medicine, Division of Infectious Diseases, U.C. Irvine Medical Center, 101 The City Dr., Orange CA 92668 USA), Immunopharmacology 1997, 35(3), pp. 229-235, Elsevier. (Abstract only).

Chemical Abstract No. 127: 351175q, *Pharmaceutical Grade Botanical Drugs*, Khwaja, Tasneem A.; Friedman, Elliot P. (Friedmann, Elliot P.; Khwaja, Tasneem A.; Pharmaparint, Inc.; University of Southern California, USA) PCT Int. Appl. WO 97 39,355 Oct. 23, 1997, US Appl. 623,273, Apr. 15, 1996; 222 pp. (Abstract only).

Chemical Abstract No. 129: 14170z, *Gas Chromatography-Mass Spectral Analysis of Roots of Echinacea Speices and Classification by Multivariate Data Analysis*, Lienert, Doris; Anklam, Elke; Panne, Ulrich (Joint Research Centre Inspra, Commission of the European Union, Environment Institute, I-21020 Ispra, Italy), Phytochem. Anal. 1998, 9(2), pp. 88-98, John Wiley & Sons Ltd. (Abstract only).

Chemical Abstract No. 130: 316594r, *Pharmaceutical Grade Echinaccea*, Khwaja, Tasneem A.; Friedman, Elliot P. (Pharmaprint, Inc.; University of Southern California, USA) PCT Int. Appl. WO 99 21,007, Apr. 29, 1999, US Appl. 956,603, Oct. 23, 1997; 70 pp. (Abstract only).

Kuo-Hsiung Lee, "Anticancer Drug Design Based on Plant-Derived Natural Products", Journel of Biomedical Science 1999; 6:236-250, Natural Products Laboratory, Division of Medicinal Chemistry and Natural Products, School of Pharmacy, University of North Carolina, Chapel Hill, N.C., USA.

\* cited by examiner

*ECHINACEA* INDUCTION OF PHASE II ENZYMES

BACKGROUND OF THE INVENTION

The present invention relates to the use of *Echinacea* as a cancer chemopreventive agent to block the formation of and to detoxify cancer-causing agents, or carcinogens. More particularly, the present invention relates to the induction of phase II enzymes by *Echinacea*, and specifically by lipid-soluble fractions isolated from *Echinacea*. The present invention relates to the use of lipid-soluble fractions isolated from *Echinacea* as nutritional supplements. The present invention also contemplates a novel method of extracting the desired lipid-soluble fractions from *Echinacea*.

Phase II enzymes are involved in the detoxification of cancer-causing agents by converting carcinogenic substances into products that are no longer harmful. Unexpectedly, certain fractions of *Echinacea*, particularly the lipid-soluble fractions, show a greater induction of phase II enzymes than other fractions. It is desirable to use these lipid-soluble fractions as a dietary supplement because they are the most potent and can yield the greatest benefit for cancer prevention.

*Echinacea* contains numerous active phytochemicals that have immunomodulatory and other beneficial activities. There is a long tradition of the use of *Echinacea* preparations in the adjuvant therapy of inflammations (see, Tragni et al., Evidence from two classic irritation tests for an anti-inflammatory action of a natural extract, *Echinacea B.*, *Food Chem. Toxicol.*, 23(2): 317–319 (1985); and Facino et al., Direct characterization of caffeoyl esters with antihyaluronidase activity in crude extracts from *Echinacea angustifolia* roots by fast atom bombardment tandem mass spectrometry, *Farmaco*, 48(10): 1447–1461 (1993)), skin damage (see, Facino et al., Echinacoside and caffeoyl conjugates protect collagen from free radical-induced degradation: a potential use of *Echinacea* extracts in the prevention of skin photodamage, *Planta Med.*, 61(6): 510–514 (1995)), and, more typically, infections (see, Steinmuller et al., Polysaccharides isolated from plant cell cultures of *Echinacea purpurea* enhance the resistance of immunosuppressed mice against systemic infections with *Candida albicans* and *Listeria monocytogenes*, *Int. J. Immunopharmacol.*, 15(5): 605–614 (1993)). The *Echinacea* plant is a popular herbal immunostimulant. The ability of *Echinacea* to stimulate the immune system in a nonspecific manner is exemplified in the enhancement of phagocytosis seen in cells treated with *Echinacea* (see, Sun et al., The American coneflower: a prophylactic role involving nonspecific immunity, *J. Altern. Complement Med.*, 5(5): 437–446 (1999)). *Echinacea*'s immunomodulatory activity has been attributed to various actives, including alkylamides, phenolics, polysaccharides, alkaloids, glycoproteins, and flavonoids (see, Bauer, R. and Wagner, H., *Echinacea* species as potential immunostimulatory drugs, in *Economic and Medicinal Plant Research*, Ch. 8, p. 253, Wagner, H. and Farnsworth, N. R. (Editors), Academic Press Limited, New York, N.Y., (1991)).

Phase II enzymes are a class of enzymes that detoxify cancer-causing agents and protect cells against neoplasia and mutagenesis. Phase II enzymes are thought to act by detoxifying highly reactive intermediates of carcinogens activated by Phase I enzymes. Phase II enzymes include NAD(P)H quinone reductase (quinone reductase or QR) and glutathione S-transferases (GST). The consumption of vegetables, especially crucifers, such as broccoli (Zhang et al., A major inducer of anticarcinogenic protective enzymes from broccoli: isolation and elucidation of structure, *Proc. Natl. Acad. Sci., USA.*, 89(6): 2399–2403 (1992)) and broccoli sprouts (Fahey, et al., Broccoli sprouts: an exceptionally rich source of inducers of enzymes that protect against chemical carcinogens, *Proc. Natl. Acad. Sci. USA*, 94: 10367–10372 (1997)) has been associated with the induction of phase II enzymes. Broccoli contains high levels of the compound sulforaphane which has been shown to be a potent inducer of phase II enzymes.

The ability of a compound or compounds to induce phase II enzymes can be measured by monitoring the increase in the activity of the phase II enzyme quinone reductase (QR). The induction of quinone reductase can be tested using a cell culture system similar to that developed by Prochaska et al. (Prochaska, H. J. and Santamaria, A. B., Direct Measurement of NAD(P)H:quinone reductase from cells cultured in microtiter wells: a screening assay for anticarcinogenic enzyme inducers, *Anal. Biochem.*, 169(2): 328–336 (1988)) which is incorporated herein by reference. This system measures the elevation of quinone reductase, thus detecting the potency of the phase II enzyme inducers.

SUMMARY OF THE INVENTION

The present invention is directed to the use of *Echinacea* as a cancer chemopreventive agent, and more particularly to the induction of phase II enzymes by various *Echinacea* fractions. More specifically, the present invention relates to the use of lipid-soluble fractions isolated from *Echinacea* as nutritional supplements. The present invention also contemplates a novel method of extracting the desired lipid-soluble fractions from *Echinacea*.

The term "*Echinacea*" is used to refer to any species of *Echinacea*. Presently preferred, however, is *Echinacea purpurea* which is used in the experiments described herein. Nevertheless, the contemplated scope of present invention includes any *Echinacea* species.

The terms "induction" and "induce" (e.g., induction of phase II enzymes) refer to an increase of the total measurable activity of an enzyme. The induction may occur at one level or multiple levels of gene expression or regulation. For example, induction may occur through increased transcription or translation which may lead to an increase in the total amount of an enzyme. Alternatively, induction may occur at the level of enzyme activity, where the total amount of protein does not change substantially, but the activity of the enzyme increases.

The terms "phase II enzyme" and "phase II enzymes" refer to a class of enzymes that are coupled with Phase I enzymes in detoxify cancer-causing agents. Examples of phase II enzymes include, but are not limited to, NAD(P)H quinone reductase (quinone reductase or QR), glutathione S-transferases, and UDP-glucuronosyltransferases.

The term "quinone reductase" refers to NAD(P)H quinone reductase and is abbreviated "QR". These terms refer to the same enzyme and are used interchangeably.

The term "MTT" is an abbreviation for 3-(4,5-dimethylthiazo-2-yl)-2,5-diphenyltetrazolium bromide.

DETAILED DESCRIPTION OF THE PREFERRED EMBODIMENTS

Figure 1:
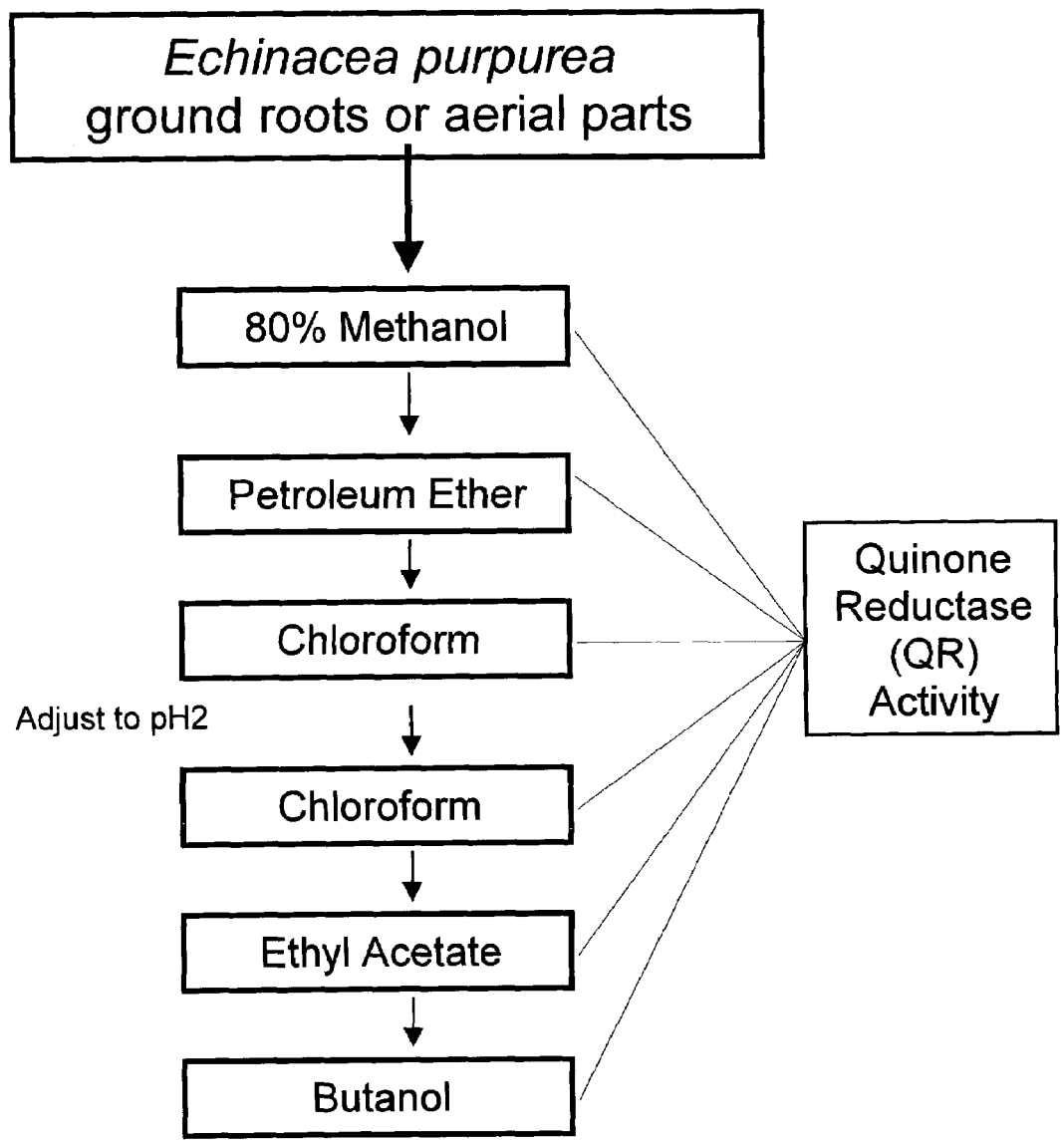
FIG. 1 is a flow chart of the extraction procedure.

In accordance with the present invention, a cancer chemopreventive agent comprising *Echinacea* extract is provided to induce phase II enzymes. The present invention further provides a method of inducing phase II enzymes with *Echinacea* fractions. The induction of phase II enzymes has extremely important implications for human health due to the activity of these enzymes in the detoxification of potential carcinogens. The detection of phase II enzyme induction is used as a method to screen for anticarcinogenic compounds.

*Echinacea purpurea* fractions have been found to induce the expression of phase II enzymes. Phase II enzymes are a class of enzymes that detoxify cancer-causing agents and protect cells against neoplasia and mutagenesis. Induction of phase II enzymes is correlated with cancer chemopreventive activity. The potency of a compound or compounds for induction of phase II enzymes can be quantified by measuring the increased activity of the phase II enzyme, quinone reductase.

Studies were conducted to test for the induction of a phase II enzyme by extracted fractions of *Enchinacea purpurea* in normal rat liver cells. The cell line used was ATCC CRL-1439, obtained from the American Type Culture Collection. The CRL-1439 cell line is generally used for in vitro studies of carcinogenesis and for screening of nutritional supplements.

A compound's ability to induce phase II enzymes in vitro is indicative of the compound's activity for the induction of such enzymes in vivo. Compounds are generally screened for anti-cancer activity in vitro by growing established cell lines in the presence of the compound to be screened.

In summary, fractions from both the roots and the aerial parts of *Echinacea* were tested for induction of quinone reductase, and both root fractions and aerial part fractions induced the phase II enzyme, quinone reductase. The fractions that showed the greatest induction of quinone reductase for both the roots and the aerial parts were the lipid-soluble fractions. For the roots, the fraction with the greatest induction activity was chloroform fraction (1). (See FIG. 2). For the aerial parts, the fraction with the greatest induction activity is acidic chloroform fraction (2). (See FIG. 2).

For the roots, the level of enzyme activity in the root chloroform fraction (1) was 35% higher than the root 80% methanol fraction. Likewise, for the aerial parts, the level of enzyme activity in the acidic chloroform fraction (2) was 87% higher than the more polar fraction extracted with 80% methanol. The fractions that showed the greatest induction of phase II enzymes for *Echinacea* were, therefore, the lipid soluble fractions.

Extraction Procedure

Generally, the extraction procedure provides a method of producing lipid-soluble solids of harvested *Echinacea* plant material. *Echinacea* plant material is chopped and dehydrated. The dehydrated plant material is then extracted with aqueous methanol, filtered, and dried to produce a dried methanol extract. At least a portion of the dried methanol extract is mixed with water to provide an aqueous suspension. The aqueous suspension is fractionated with petroleum ether to provide a petroleum ether fractionated aqueous layer and an organic petroleum ether layer. The organic petroleum ether layer is collected and dried to provide a dried petroleum ether fraction. The petroleum ether fractionated aqueous layer is further fractionated with chloroform to provide a chloroform fractionated aqueous layer and an organic chloroform layer. The organic chloroform layer is collected and dried to provide a dried chloroform fraction (chloroform fraction (1) in FIG. 2). The chloroform fractionated aqueous layer is then adjusted to a pH level of about pH 2 to provide a pH-adjusted chloroform fractionated aqueous layer. The pH-adjusted chloroform fractionated aqueous layer is further fractionated with chloroform to provide an acidic chloroform fractionated aqueous layer and an acidic organic chloroform layer. The acidic organic chloroform layer is collected and dried to provide a dried acidic chloroform fraction (acidic chloroform fraction (2) in FIG. 2). The acidic chloroform fractionated aqueous layer is further fractionated with ethyl acetate to provide an ethyl acetate fractionated aqueous layer and an organic ethyl acetate layer. The organic ethyl acetate layer is collected and dried to provide a dried ethyl acetate fraction. The ethyl acetate fractionated aqueous layer is further fractionated with butanol to provide a butanol fractionated aqueous layer and an organic butanol layer. The organic butanol layer is collected and dried to provide a dried butanol fraction.

In greater detail, the extraction procedure was carried out as follows. Whole full-bloom plants of *Echinacea purpurea* were manually harvested. After harvesting, the roots and the aerial parts were separated, chopped by hand, and dehydrated at 60° C. Samples were stored separately in cool, dark conditions until the extraction was carried out.

The roots and the aerial parts of the plant were separated and were kept separate throughout the extraction procedure. Therefore, each sample discussed is either a root sample or an aerial part sample, not a mixture of root and aerial parts. The same procedure, as described below and as shown in FIG. 1, was used for the extraction and fractionation of the roots and the aerial parts of *Echinacea purpurea*.

Dehydrated roots or aerial parts of *Echinacea purpurea* were blended with a Warning commercial laboratory blender (Warning model 34BL79). 100 g of blended material then was extracted with 500 ml of 80% methanol under reflux in a water bath for 50 minutes. The extraction solution was filtered immediately. The 80% methanol extraction procedure was then repeated. The two 80% methanol root extraction solutions were combined and the two 80% methanol aerial extraction solutions were combined. Each was evaporated to dryness by a vacuum rotary evaporator at about 30° to 40° C.

The total amount of dried extract obtained from the 80% methanol extraction was approximately 11.7 g of roots and approximately 20.5 g of aerial parts. From these total amounts of dried extract, 5.8 g of the root extract and 10.3 g of the aerial part extract were used to continue the fractionation procedure. These gram amounts of extract (5.8 g of root extract and 10.3 g of aerial part extract) were designated as 100% for the purpose of calculating the percentage yield from subsequent fractionation steps.

The 5.8 g of root extract and the 10.3 g of aerial part extract were each suspended in 100 ml of water. The suspensions were fractionated, in sequence, three times with 100 ml of petroleum ether, and then three times with 100 ml of chloroform (referred to as "chloroform (1)" fraction). The organic layers from the fractionations were collected and combined as described below. The aqueous layers were used for the subsequent fractionation. The three petroleum ether root fractions were combined, and the three chloroform (1) root fractions were combined. Similarly, the three petroleum ether aerial fractions were combined, and the three neutral chloroform aerial fractions were combined. The fractions were then dried over anhydrous sodium sulfate, then filtered, and evaporated to dryness. The yield from the petroleum ether fractions was 0.100 g roots (1.71%) and 0.158 g aerial parts (1.55%). The yield from the chloroform (1) fractions was 0.238 g roots (4.11%) and 0.219 g aerial parts (2.14%).

The aqueous layers of the root extract and the aerial part extract were adjusted to pH 2 with 2N HCl and were re-extracted, in sequence, three times with 100 ml of chloroform (referred to as the "acidic chloroform (2)" fraction), three times with 100 ml of ethyl acetate, and three times with 100 ml of butanol. The three acidic chloroform (2) root fractions were combined, the three ethyl acetate root fractions were combined, and the three butanol root fractions were combined. Similarly, the three acidic chloroform (2) aerial fractions were combined, the three ethyl acetate aerial fractions were combined, and the three butanol aerial fractions were combined.

The collected organic layers were washed twice with water using 50 ml of water for each wash. The washed organic layers were then dried over anhydrous sodium sulfate, then filtered, and evaporated to dryness by a vacuum rotary evaporator at about 30 to 40° C. The yield from the acidic chloroform (2) fraction was 0.054 g roots (0.92%) and 0.044 g aerial parts (0.43%). The yield from the ethyl acetate fraction was 0.619 g roots (10.7%) and 0.330 g aerial parts (3.23%). The yield from the butanol fraction was 0.061 g roots (1.05%) and 0.063 g aerial parts (0.62%).

The six fractions, or test extracts, (80% methanol, petroleum ether, chloroform (1), acidic chloroform (2), ethyl acetate, and butanol) were stored in a refrigerator at approximately 4° C. until the enzyme assays were performed. The test extracts were redissolved with $\alpha$-MEM prior to analysis and their concentrations were recorded in mg/ml.

Quinone Reductase Assay

The quinone reductase assay is modified from the method described by Prochaska, H. J. and Santamaria, A. B., Direct Measurement of NAD(P)H:Quinone Reductase from Cells Cultured in Microtiter Wells: A Screening Assay for Anticarcinogenic Enzyme Inducers, *Analytical Biochemistry*, 169: 328–336 (1988), which is incorporated herein by reference.

Generally, the assay measures quinone reductase activity in catalyzing a NADPH-dependent menadiol-mediated reduction of MTT to a blue formazan dye. Liver cells are exposed to a test extract in medium or, in the case of the controls, the cells are exposed to medium only. When the cells are subsequently broken, the quinone reductase is released. A reaction cocktail containing glucose-6-phosphate and glucose-6-phosphate dehydrogenase, which together continually generate NADPH, is added to the cell samples. Quinone reductase, which is the only rate limiting step, uses NADPH to transfer electrons to menadione converting it to menadiol. The menadiol then reduces MTT to form the blue formazan dye. This blue tint is measured at 610 nm on a Microtiterplate Reader equipped with a data processor (Model # Vmax Kinetic Microplate Reader—Molecular Devices equipped w/Softmax software).

More specifically, normal rat liver cells (ATCC CRL-1439) were cultured in a $\alpha$-MEM (minimal essential medium) at 37° C. in a 6% $CO_2$ incubator with 98% humidity. Cells were trypsinized and plated in 96-well microtiter plates at a density of about 3000 cells per well. The cells were grown for 24 hours and were attached to the bottom of the well. The medium was changed when the test extracts were added. In the case of the controls, only medium was added. After growing for 48 hours, the medium was shaken off of the 96 well plates. Then the cells were lysed by incubation with a 0.4% digitonin solution. The reaction cocktail was then added to the cells and the blue color was allowed to develop. The reaction was arrested, and the optical density of the samples was read at 610 nm. The quinone reductase activity of the samples was calculated by dividing the optical density of the cells treated with test extracts by the optical density of the untreated cells, also known as control cells. Each concentration of extract was tested four times, so four wells were used for each concentration of extract (Note: This protocol is modified from the Prochaska et al. protocol in which cells are exposed to test compounds for 24 hours.)

Figure 2:
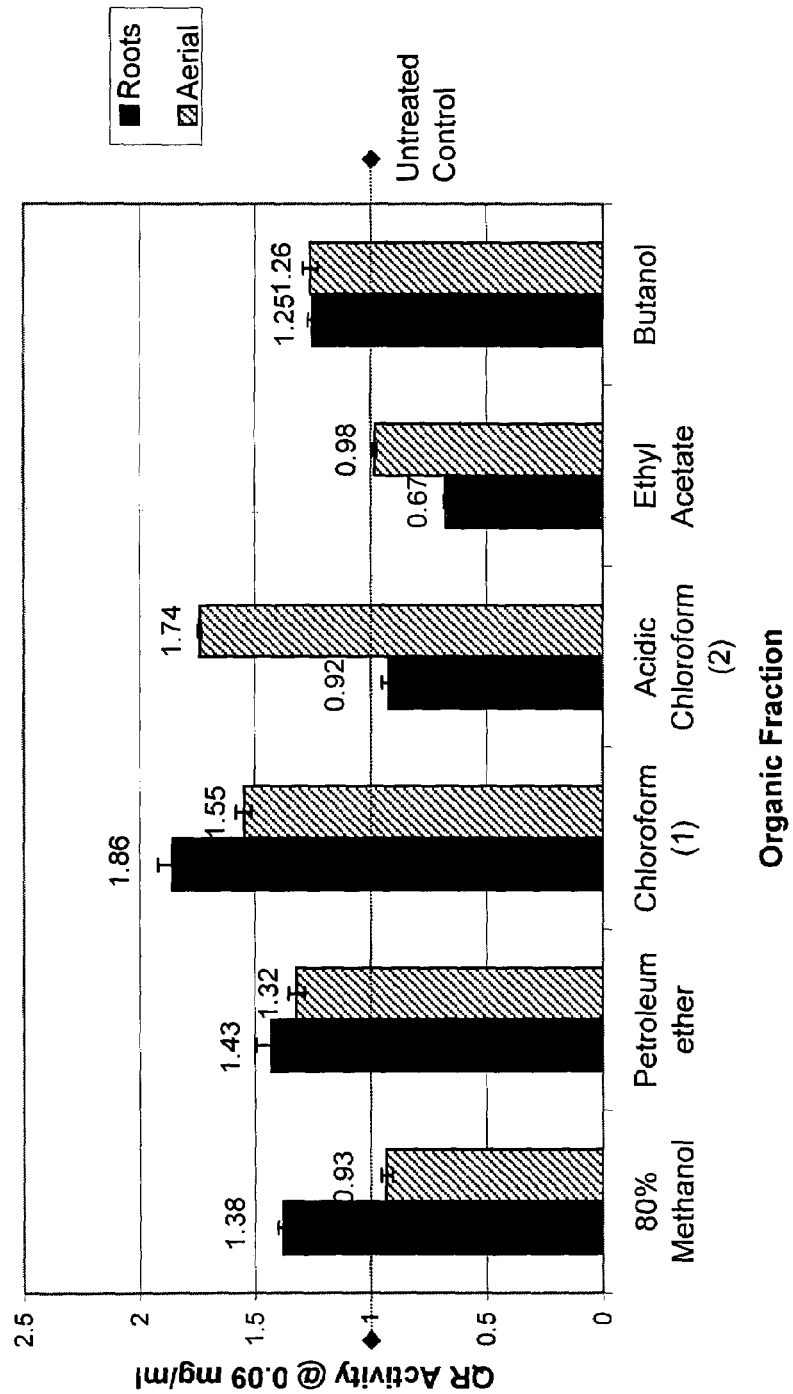
FIG. 2 is a bar graph of the Quinone Reductase Activity of *Echinacea purpurea* Root and Aerial Fractions.

The results of the quinone reductase induction experiments are shown in FIG. 2. FIG. 2 is a bar graph that illustrates the quinone reductase induction activity of each of the six fractions for both roots and aerial parts at a set concentration of 0.09 mg/ml extract. In FIG. 2, each data point represents the mean of 4 replications, plus or minus the standard error of the mean. At this concentration of extract, the root fraction with the greatest quinone reductase induction activity was the chloroform (1) fraction with activity at 1.86 times the level of the control. The aerial parts fraction with the greatest quinone reductase induction activity was the acidic chloroform (2) fraction with activity at 1.74 times that of control. For the roots, the level of enzyme activity in the root chloroform (1) fraction was 35% higher than the root 80% methanol fraction. Likewise, for the aerial parts, the level of enzyme activity in the acidic chloroform (2) fraction was 86% higher than the more polar fraction extracted with 80% methanol.

The fractions that showed the greatest induction of quinone reductase for both the roots and the aerial parts are lipid soluble fractions. These fractions have the greatest potency for the induction of phase II enzymes and for chemopreventive activity.

Administration of therapeutic compositions according to the present invention can be via any common route, including, for example, oral, nasal, or topical. Alternatively, administration can be by orthotopic, intradermal, subcutaneous, intramuscular, intraperitoneal or intravenous injection. Dosage forms include, but are not limited to, tablets, capsules, caplets, dietary bar, solution, suspension gel, powder, cream, transdermal patch, and implanting reservoir. Such compositions can normally be administered as nutritionally acceptable compositions that include physiologically acceptable carriers, buffers, or other excipients. Compositions for oral administration may contain acceptable carriers, for example, mannitol, lactose, starch, magnesium stearate, sodium saccharine, cellulose, magnesium carbonate, and the like.

The nutritional supplements of the present invention may be formulated using any pharmaceutically acceptable forms of the extracts discussed above, including their salts. Preferred forms include calcium carbonate, magnesium hydroxide or magnesium sulfate, sodium tetraborate, cupric oxide, manganese sulfate, zinc sulfate, cholecalciferol, ferrous fumarate, pyridoxine hydrochloride, chromium picolinate, and ascorbic acid. The dietary supplements may be formulated for mixing with consumable liquids such as milk, juice, water or consumable gels or syrups for mixing into other dietary liquids or foods. The dietary supplements of this invention may be formulated with other foods or liquids to provide premeasured supplemental foods, such as single serving bars, for example. Flavorings, binders, protein, complex carbohydrates, and the like may be added as needed.

The dietary supplements of the present invention can be formulated for once-daily administration. Alternatively, they can be formulated in multiple portions or as time release compositions for more or less frequent administration.

Although the description above contains many specifics, these should not be construed as limiting the scope of the invention, but as merely providing illustrations of some of the presently preferred embodiments of this invention. Thus the scope of this invention should be determined by the appended claims and their legal equivalents, rather than by the examples given.

What is claimed:

1. A method of inducing the expression of a phase II enzyme in a mammal comprising administering to the mammal a therapeutically effective amount of a a chloroform-soluble *Echinacea purpurea* fraction selected from the group consisting of a chloroform root fraction, an acidic chloroform aerial fraction, and a combination thereof.

2. The method of claim 1 wherein the chloroform-soluble *Echinacea* fraction is provided in a concentration of about 0.09 mg of the fraction per ml of a medium.

3. The method of claim 1 wherein the phase II enzyme has a quinone reductase activity of about 1.86 at 610 nm.

* * * * *